US006997870B2

(12) United States Patent
Couvillon, Jr.

(10) Patent No.: US 6,997,870 B2
(45) Date of Patent: *Feb. 14, 2006

(54) UNIVERSAL, PROGRAMMABLE GUIDE CATHETER

(75) Inventor: Lucien Alfred Couvillon, Jr., Concord, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/751,544

(22) Filed: Jan. 5, 2004

(65) Prior Publication Data

US 2004/0143160 A1 Jul. 22, 2004

Related U.S. Application Data

(63) Continuation of application No. 10/176,977, filed on Jun. 21, 2002, now Pat. No. 6,679,836.

(51) Int. Cl.
*A61B 1/00* (2006.01)
(52) U.S. Cl. .................................. 600/146; 600/151
(58) Field of Classification Search ................ 600/114, 600/117, 143, 145, 146, 151, 152; 604/95.01
See application file for complete search history.

(56) References Cited

U.S. PATENT DOCUMENTS

| 4,273,111 A | 6/1981 | Tsukaya ........................ 128/6 |
| 4,286,585 A | 9/1981 | Ogawa .......................... 128/6 |
| 4,499,895 A | 2/1985 | Takayama ...................... 128/6 |
| 4,503,842 A | 3/1985 | Takayama ...................... 128/4 |
| 4,543,090 A | 9/1985 | McCoy ........................ 604/95 |
| 4,601,705 A | 7/1986 | McCoy ........................ 604/95 |
| 4,753,223 A | 6/1988 | Bremer ......................... 128/4 |
| 4,790,624 A | 12/1988 | Van Hoye et al. ........ 350/96.26 |
| 4,846,573 A | 7/1989 | Taylor et al. ................ 356/241 |
| 4,884,557 A | 12/1989 | Takehana et al. .............. 128/4 |
| 4,899,731 A | 2/1990 | Takayama et al. ............. 128/4 |
| 4,930,494 A | 6/1990 | Takehana et al. .............. 128/4 |
| 4,977,886 A | 12/1990 | Takehana et al. .............. 128/4 |
| 4,987,314 A | 1/1991 | Gotanda et al. ............ 250/551 |
| 5,090,956 A | 2/1992 | McCoy ........................ 604/95 |

(Continued)

FOREIGN PATENT DOCUMENTS

EP  0943402 A2  9/1999

(Continued)

OTHER PUBLICATIONS

Jae-Do Nam, "Electroactive Polymer (EAP) Actuators and Devices for Micro-Robot Systems"Nov. 28, 2000.
"Snake-like Robot Endoscopes", from http://robby.Caltech.edu/~chen/res-medical.html, page undated Aug. 14, 1996.

(Continued)

*Primary Examiner*—Beverly M. Flanagan
*Assistant Examiner*—Aaron Roane
(74) *Attorney, Agent, or Firm*—Mayer & Williams PC; David B. Bonham, Esq.; Keum J. Park, Esq.

(57) ABSTRACT

A guide catheter apparatus that comprises the following: (a) a guide catheter portion that includes a plurality of electroactive polymer actuators disposed along its axial length and (b) a control unit coupled to the actuators and sending control signals to the actuators. The actuators change the shape of the guide catheter portion based upon the control signals that are received from the control unit. In another aspect of the present invention, a method of introducing a guide catheter into a body lumen is provided. The method comprises: (a) providing a guide catheter apparatus like that above, and (b) inserting the guide catheter portion of the guide catheter apparatus into the body lumen, while using the control unit to control the shape of the guide catheter portion.

25 Claims, 11 Drawing Sheets

U.S. PATENT DOCUMENTS

| | | | |
|---|---|---|---|
| 5,188,111 A | 2/1993 | Yates et al. ................ | 128/657 |
| 5,239,982 A | 8/1993 | Trauthen ...................... | 128/4 |
| 5,250,167 A | 10/1993 | Adolf et al. ............... | 204/299 |
| 5,268,082 A | 12/1993 | Oguro et al. ............... | 204/282 |
| 5,337,732 A | 8/1994 | Grundfest et al. ............ | 128/4 |
| 5,347,987 A | 9/1994 | Feldstein et al. ............. | 128/4 |
| 5,368,015 A | 11/1994 | Wilk ............................ | 128/4 |
| 5,389,222 A | 2/1995 | Shahinpoor ............. | 204/299.2 |
| 5,396,879 A | 3/1995 | Wilk et al. ..................... | 128/4 |
| 5,431,645 A | 7/1995 | Smith et al. ................... | 606/1 |
| 5,482,029 A | 1/1996 | Sekiguchi et al. ......... | 600/109 |
| 5,486,182 A | 1/1996 | Nakao et al. ............... | 606/114 |
| 5,492,131 A | 2/1996 | Galel ......................... | 128/772 |
| 5,535,759 A * | 7/1996 | Wilk .......................... | 128/898 |
| 5,556,370 A | 9/1996 | Maynard ................... | 600/151 |
| 5,556,700 A | 9/1996 | Kaneto et al. ............. | 428/332 |
| 5,624,380 A * | 4/1997 | Takayama et al. ......... | 600/146 |
| 5,631,040 A | 5/1997 | Takuchi et al. ............ | 427/100 |
| 5,645,520 A | 7/1997 | Nakamura et al. ......... | 600/151 |
| 5,651,366 A | 7/1997 | Liang et al. ........... | 128/662.06 |
| 5,662,587 A | 9/1997 | Grundfest et al. ......... | 600/114 |
| 5,771,902 A | 6/1998 | Lee et al. .................. | 128/897 |
| 5,819,749 A | 10/1998 | Lee et al. | |
| 5,855,565 A | 1/1999 | Bar-Cohen et al. ........ | 604/104 |
| 5,857,962 A | 1/1999 | Bracci et al. .............. | 600/105 |
| 5,873,817 A | 2/1999 | Kokish et al. ............. | 600/143 |
| 5,906,591 A | 5/1999 | Dario et al. ................. | 604/95 |
| 5,916,146 A | 6/1999 | Allotta et al. .............. | 600/141 |
| 5,957,833 A * | 9/1999 | Shan ......................... | 600/117 |
| 6,071,234 A | 6/2000 | Takada ...................... | 600/114 |
| 6,109,852 A | 8/2000 | Shahinpoor et al. ........... | 414/1 |
| 6,117,296 A | 9/2000 | Thomson ................... | 204/607 |
| 6,162,171 A | 12/2000 | Ng et al. ................... | 600/141 |
| 6,249,076 B1 * | 6/2001 | Madden et al. ............ | 310/363 |
| 6,428,470 B1 | 8/2002 | Thompson ................. | 600/173 |
| 6,468,203 B2 * | 10/2002 | Belson ....................... | 600/146 |
| 6,514,237 B1 | 2/2003 | Maseda ...................... | 604/533 |
| 6,547,723 B1 | 4/2003 | Ouchi ........................ | 600/146 |
| 6,679,836 B2 * | 1/2004 | Couvillon, Jr. ............ | 600/146 |

FOREIGN PATENT DOCUMENTS

| | | |
|---|---|---|
| ES | 2 048 086 | 1/1992 |
| ES | 2 062 930 | 12/1992 |
| FR | 2732225 | 10/1996 |
| JP | 3004830 | 1/1991 |
| JP | 3170125 | 7/1991 |
| JP | 05177002 | 7/1993 |
| JP | 8066351 | 3/1996 |
| JP | 8322783 | 12/1996 |
| JP | 10014863 | 1/1998 |
| WO | WO 99/60267 | 11/1999 |
| WO | WO 01/58973 A2 | 8/2001 |

OTHER PUBLICATIONS

Peirs et al., "Miniature Parallel Manipulators for Integration in a Self-propelling Endoscope," IUAP P4/24 IMechS Workshop, Oct. 27, 1999.

"Walking machines: 0-legged-robots," compiled by C. Duntgen, Aug. 26, 2000.

Yoseph Bar-Cohen, Ed., Electroactive Polymer (EAP) Actuators as Artificial Muscles, SPIE Press (2001), Chapter 1, pp. 3-44.

Yoseph Bar-Cohen, Ed., Electroactive Polymer (EAP) Actuators as Artifical Muscles, SPIE Press (2001), Chapter 7, pp. 193-221.

Jeón et al., Smart Structures and Materials 2001: Electroactive Polymer Actuators and Devices, Yoseph Bar-Cohen, Ed., Proceedings of SPIE vol. 4329 (Mar. 5-8, 2001), pp. 380-388.

Cho et al., Smart Structures and Materials 2001: Electroactive Polymer Actuators and Devices, Yoseph Bar-Cohen, Ed., Proceedings of SPIE vol. 4329 (Mar. 5-8, 2001), pp. 466-474.

Kubler et al., "An Endoscopic Navigation System," Proceedings of Medicine Meets Virtual Reality—MMVR 2001, pp. 253-255.

Kubler et al., "Endoscopic Robots," Proceedings of 3rd International Conference on Medical Image Computing and Computer-Assisted Intervention—MICCAI 2000, pp. 949-955.

Worldwide ElectroActive Polymers (Artificial Muscles) Newsletter, vol. 3, No. 1 (Jun. 2001).

"Smart Catheters," from http://www.piaggio.ccii.unipi.it/cathe.htm, printed Aug. 27, 2001.

"Snake-like Flexible Micro-robot," from http://www.agip.sciences.univ-metz.fr/~mihalach/Copernicus_project_engl.html, Project start: May 1, 1995.

"Robot Snake with Flexible Real-Time Control," from http://ais.gmd.de/BAR/snake.html, last updated Jan. 10, 1917.

Jager et al., "Microfabricating Conjugated Polymer Actuators," Science, vol. 290 (Nov. 24, 2000), pp. 1540-1545.

Electroactive Polymer (EAP) Actuators as Artifical Muscles, Yoseph Bar-Cohen, Ed., SPIE Press (2001), Chapter 16, pp. 457-495.

Electroactive Polymer (EAP) Actuators as Artifical Muscles, Yoseph Bar-Cohen, Ed., SPIE Press (2001), Chapter 21, pp. 615-659.

Yoseph Bar Cohen, Smart Structures and Materials 2001; Electroactive Polymer Actuators and Devices, Yoseph Bar-Cohen, Ed., Proceedings of SPIE vol. 4329 (Mar. 5-8, 2001), pp. 1-6.

Madden et al., Smart Structures and Materials 2001: Electroactive Polymer Actuators and Devices, Yoseph Bar-Cohen, Ed., Proceedings of SPIE vol. 4329 (Mar. 5-8, 2001), pp. 72-83.

Pelrine et al., Smart Structuues and Materials 2001: Electroactive Polymer Actuators and Devices, Yoseph Bar-Cohen, Ed., Proceedings of SPIE vol. 4329 (Mar. 5-8, 2001), pp. 335-349.

John David Wyndham Madden, "Conducting Polymer Actuators," Massachusetts Institute of Technology, Sep. 2000.

"Viking Optima," from http://www.guidant.com/products/optima.shtml, 2002 Guidant Corporation.

Active Endoscope (ELASTOR, Shape Memory Alloy Robot), http://mozu.mes.titech.ac.jp/research/medical/endoscope/endoscope.html, 9 pages including 3 Figures and 4 photographs.

Koji Ikuta et al., "Shape Memory Alloy Servo Actuator System With Electric Resistance Feeback And Application For Active Endoscope," IEEE Int'l Conference on Robotics and Automation (Apr. 24-29, 1988), pp. 427-430.

David L. Brock, "Review of Artificial Muscle based on Contractile Polymers," MIT Artificial Intelligence Laboratory, A.I. Memo No. 1330, Nov. 1991, pp. 1-12.

A. Della Santa et al., "Intravascular Microcatheters Steered by Conducting Polymer Actuators," 18th Annual International Conference of the IEEE Engineering in Medicine and Biology Society, Amsterdam 1996, pp. 2203-2204.

Alberto Mazzoldi et al., "Conductive Polymer Based Structures for a Steerable Catheter," *Smart Structures and Materials 2000: Electroactive Polymer Actuators and Devices*, Y. Bar-Cohen, ed., Proceedings of SPIE, vol. 3987 (2000), pp. 273-280.

* cited by examiner

UNIVERSAL, PROGRAMMABLE GUIDE CATHETER

STATEMENT OF RELATED APPLICATION

This is a continuation of U.S. patent application Ser. No. 10/176,977, filed Jun. 21, 2002, and entitled "Universal, Programmable Guide Catheter," now issued as U.S. Pat. No. 6,679,836.

FIELD OF THE INVENTION

The present invention relates to guide catheters, and more particularly to guide catheters whose shape and/or stiffness can be tailored to a patient through programmed control.

BACKGROUND OF THE INVENTION

Guide catheters are used routinely in medical procedures, including coronary and other cardiac and vascular procedures. Guide catheters provide a channel through which suitable interventional devices, for example, angioplasty devices, stent delivery catheters, electrophysiology catheters, and so forth, can be introduced, and through which radiographic contrast dye can be injected.

In use, the guide catheter is typically advanced through a valved introducer fitting, up the arteries or veins of the leg or arm, to a desired treatment location (e.g., the heart), where its tip, which is generally soft, is placed against or otherwise near the region to be treated (e.g., the coronary ostium). The catheter should provide good channel integrity and torque response as the catheter is advanced, and should provide good support as the interventional device is advanced. Guide catheters are sold in a variety of preformed sizes and shapes, which are based on years of custom and experienced ranges of patient anatomy. If one guide catheter does not give access or provide enough support, a different guide catheter is typically substituted from a large inventory of guide catheters having various shapes and sizes.

SUMMARY OF THE INVENTION

The present invention is directed to a novel guide catheter having electroactive polymer actuators integrated into the guide catheter structure.

According to a first aspect of the present invention, a guide catheter apparatus is provided, that comprises the following: (a) a guide catheter portion that includes a plurality of electroactive polymer actuators disposed along its axial length and (b) a control unit coupled to the actuators and sending control signals to the actuators. Based upon the control signals received from the control unit, the actuators change the shape of the guide catheter portion. If desired, the guide catheter portion can further comprise a plurality of strain gauges for electronic feedback.

The electroactive polymer actuators are beneficially provided over a substantial portion of the fully inserted axial length of the guide catheter portion of the present invention. For example, the electroactive polymer actuators of the guide catheters of the present invention can be disposed along 5%, 10%, 25%, 50%, 75% or more of the fully inserted length of the guide catheter portion.

The electroactive polymer actuators are preferably controllable to provide a desired curvature to the guide catheter portion at each of a plurality of loci along the length of the catheter portion, including "S" shaped, in-plane and out-of-plane curves as well as more complex, curvatures.

In some embodiments of the invention, the control signals from the control unit correspond to a user selectable shape for the guide catheter portion, which can be stored, for example, in electronic memory, if desired. In other embodiments, the control signals from the control unit are generated by a shape-generating algorithm based on medical diagnostic imaging data, for example, angiogram data. In still other embodiments, the control signals from the control unit are generated, at least in part, by a manual steering device.

In one preferred configuration, the guide catheter portion comprises a lead module and a plurality of following modules. In this configuration, when each following module reaches a position previously occupied by the lead module, the actuators cause the following module to replicate the orientation that the lead module had when it was at that particular position. Lead module orientation data can be provided, for example, by strain gauges within the lead module. Position data can be provided, for example, by a depth gauge or a linear displacement module.

In some preferred embodiments, at least a portion of the actuators are in tension with one another. This allows, for example, for the catheter to be stiffened after reaching a desired location within the body.

Each electroactive polymer actuator may beneficially comprise (a) an active member portion, (b) a counter-electrode portion and (c) a region comprising an electrolyte disposed between the active member portion and the counter-electrode portion. In preferred embodiments, the actuator further comprises a substrate layer and a barrier layer, with the active member portion, counter-electrode portion and the electrolyte region disposed between the substrate layer and barrier layer. In one specific embodiment, the substrate layer is rolled into the shape of a tube.

Preferred electroactive polymers for the practice of the present invention include polyaniline, polypyrrole, polysulfone and polyacetylene.

In some embodiments, the guide catheter portion comprises a structural element selected from the following: (a) a tubular network comprising at least one metallic filament, (b) a tubular interconnected network of articulable segments, (c) a helical structure comprising at least one metallic filament, and (d) a patterned tubular sheet (e.g., a laser cut tube).

The control unit can comprise, for example, a computer, such as a personal computer. The control unit can be coupled to the actuators in a number of ways, for example, via a multiplexed electrical cable or wireless interface.

According to another aspect of the invention, a method of introducing a guide catheter into a body lumen is provided. The method comprises: (a) providing a guide catheter apparatus like that above, and (b) inserting the guide catheter portion of the guide catheter apparatus into the body lumen while controlling the shape of the guide catheter portion using the control unit. Frequently, the method will further comprise inserting an interventional device through the guide catheter portion in order to conduct a surgical procedure.

One advantage of the present invention is that a guide catheter is provided wherein the shape and/or stiffness of the guide can be controlled along its length.

Another advantage is that hospital inventory can be reduced, because a smaller number of catheter sizes are adequate to fit all patients.

Another advantage is that productivity is increased, because the guide catheters of the present invention provide improved access to complex anatomical locations based on their ability to change shape, and because the support needed during the procedure can be readily adjusted.

These and other embodiments and advantages of the present invention will become apparent from the following detailed description, and the accompanying drawings, which illustrate by way of example the features of the invention.

DETAILED DESCRIPTION OF THE INVENTION

The present invention now will be described more fully hereinafter with reference to the accompanying drawings, in which preferred embodiments of the present invention are shown. This invention may, however, be embodied in different forms and should not be construed as limited to the embodiments set forth herein.

According to preferred embodiments of the present invention, a guide catheter is provided in which electroactive polymer actuators are integrated into the guide catheter structure. Actuators based on electroactive polymers, members of the family of plastics referred to as "conducting polymers," are preferred for the practice of the present invention, due to their small size, large force and strain, low cost and ease of integration into the guide catheters of the present invention.

Electroactive polymers are a class of polymers characterized by their ability to change shape in response to electrical stimulation. They typically structurally feature a conjugated backbone and have the ability to increase electrical conductivity under oxidation or reduction. Some common electroactive polymers are polyaniline, polysulfone, polypyrrole and polyacetylene. Polypyrrole is pictured below:

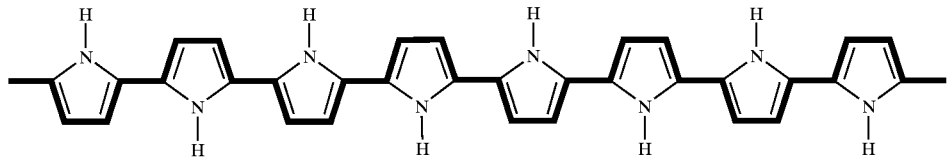

These materials are typically semi-conductors in their pure form. However, upon oxidation or reduction of the polymer, conductivity is increased. The oxidation or reduction leads to a charge imbalance that, in turn, results in a flow of ions into the material in order to balance charge. These ions, or dopants, enter the polymer from an ionically conductive electrolyte medium that is coupled to the polymer surface. The electrolyte may be, for example, a gel, a solid, or a liquid. If ions are already present in the polymer when it is oxidized or reduced, they may exit the polymer.

It is well known that dimensional changes may be effectuated in certain conducting polymers by the mass transfer of ions into or out of the polymer. For example, in some conducting polymers, the expansion is due to ion insertion between chains, whereas in others inter-chain repulsion is the dominant effect. Thus, the mass transfer of ions both into and out of the material leads to an expansion or contraction of the polymer.

Currently, linear and volumetric dimensional changes on the order of 25% are possible. The stress arising from the dimensional change can be on the order of 3 MPa, far exceeding that exerted by smooth muscle cells.

Figure 1:
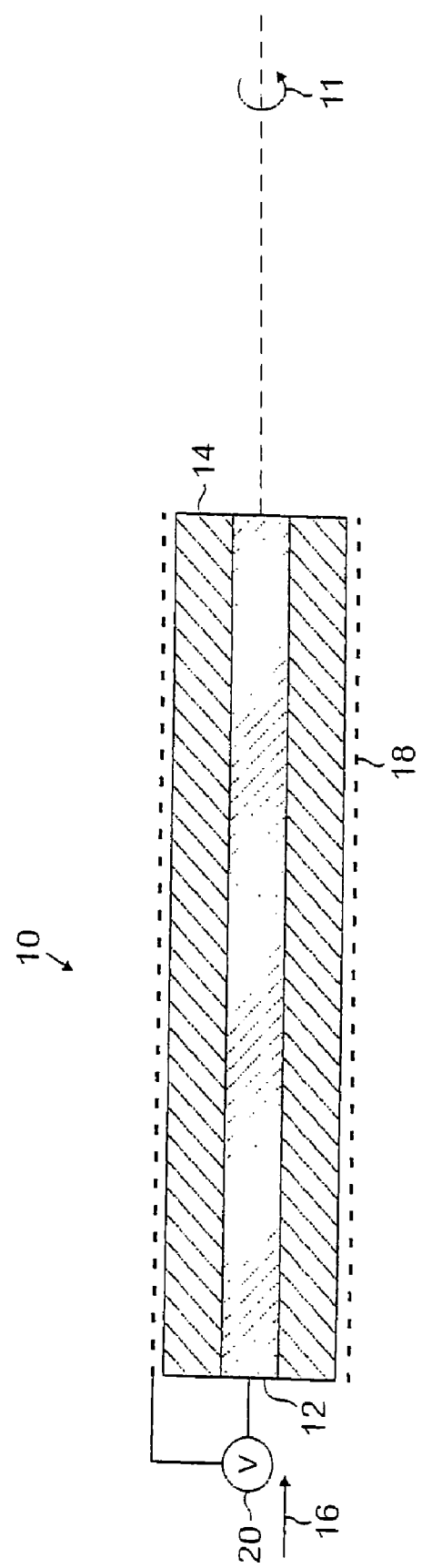
FIG. 1 is a schematic cross-sectional diagram of an electroactive polymer actuator useful in connection with the present invention.

Referring now to FIG. 1, an actuator 10 is shown schematically in cross-section. Active member 12 of actuator 10 has a surface coupled with electrolyte 14 and has an axis 11. Active member 12 includes an electroactive polymer that contracts or expands in response to the flow of ions out of, or into, the active member 12. Ions are provided by electrolyte 14, which adjoins member 12 over at least a portion, and up to the entirety, of the surface of active member 12 in order to allow for the flow of ions between the two media. Many geometries are available for the relative disposition of member 12 and electrolyte 14. In accordance with preferred embodiments of the invention, member 12 may be a film, a fiber or a group of fibers, or a combination of multiple films and fibers disposed so as to act in consort for applying a tensile force in a longitudinal direction substantially along axis 11. The fibers may be bundled or distributed within the electrolyte 14.

Active member 12 includes an electroactive polymer. Many electroactive polymers having desirable tensile properties are known to persons of ordinary skill in the art. In accordance with preferred embodiments of the invention, active member 12 is a polypyrrole film. Such a polypyrrole film may be synthesized by electrodeposition according to the method described by M. Yamaura et al., "Enhancement of Electrical Conductivity of Polypyrrole Film by Stretching: Counter-ion Effect," Synthetic Metals, vol. 36, pp. 209–224 (1988), which is incorporated herein by reference. In addition to polypyrrole, any conducting polymer that exhibits contractile or expansile properties may be used within the scope of the invention. Polyaniline is an example of such a usable conducting polymer.

Electrolyte 14 may be, for example, a liquid, a gel, or a solid, so long as ion movement is allowed. Moreover, where the electrolyte 14 is a solid, it should move with the active member 12 and should not be subject to delamination. Where the electrolyte 14 is a gel, it may be, for example, an agar or polymethylmethacrylate (PMMA) gel containing a salt dopant. Where the electrolyte is a liquid, it may be, for example, a phosphate buffer solution. The electrolyte is preferably non-toxic in the event that a leak inadvertently occurs in vivo.

Counter electrode 18 is in electrical contact with electrolyte 14 in order to provide a return path for charge to a source 20 of potential difference between member 12 and electrolyte 14. Counter electrode 18 may be any electrical conductor, for example, another conducting polymer, a conducting polymer gel, or a metal such as gold or platinum, which can be applied, for example, by electroplating, chemical deposition, or printing. In order to activate actuator 10, a current is passed between active member 12 and counter electrode 18, inducing contraction or expansion of member 12. Additionally, the actuator may have a flexible skin for separating the electrolyte from an ambient environment.

The actuators can be provided in an essentially infinite array of configurations as desired, including planar actuator configurations (e.g., with planar active members and counter-electrodes), cylindrical actuator configurations (e.g., see the actuator illustrated in FIG. 1), and so forth.

Additional information regarding the construction of actuators, their design considerations, and the materials and components that may be employed therein, can be found, for example, in U.S. Pat. No. 6,249,076, assigned to Massachusetts Institute of Technology, and in Proceedings of the SPIE, Vol. 4329 (2001) entitled "Smart Structures and Materials 2001: Electroactive Polymer and Actuator Devices (see, in particular, Madden et al, "Polypyrrole actuators: modeling and performance," at pp. 72–83), both of which are hereby incorporated by reference in their entirety.

As part of a failsafe mechanism for the devices of the present invention, it may be beneficial to select actuators that are of a type that relax in the event that power is interrupted.

Actuators are provided over a substantial portion of the fully inserted length of the guide catheters of the present invention, for example, preferably spanning at least the distal tip at which the guide catheter impinges upon the coronary ostium, for example, the most distal four centimeters or so of the guide catheter, and more preferably including the regions of the guide catheter which are shaped as it is introduced and stiffened after introduction, e.g., the region traversing the aortic arch, up to and including the fully inserted length of the guide catheter. For example, the actuators can be provided over at least 5%, and in other instances at least 10%, at least 15%, at least 20%, at least 25%, at least 35%, at least 50%, at least 75%, at least 90%, or even 100% of the fully inserted length of the guide catheter.

Hence, the shape of at least a portion of the guide catheter can be manipulated based on the shape of the body lumen into which it is inserted. Complex shapes, including "S" shapes as well as significantly more complex shapes can, accordingly, be achieved.

The actuators can be disposed within the guide catheters of the present invention in a number of ways. For example, the actuators can be separately manufactured and subsequently attached to structural elements of the guide catheters. Alternatively, multiple actuators or actuator arrays can be disposed upon a substrate layer, for example, a polymeric sheet, which is intrinsic to the structure of the guide catheter.

Figure 2:
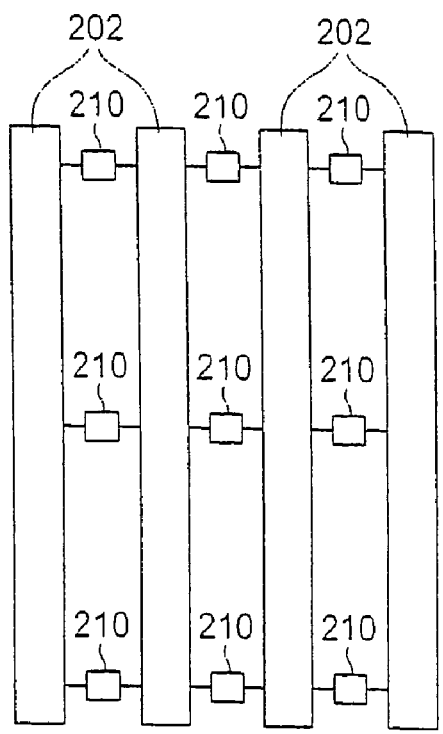
FIGS. 2–5 are schematic diagrams depicting several possible choices for the deployment of actuators with respect to structural elements in guide catheters of the present invention.

FIG. 2 illustrates one possible configuration of actuators and structural elements in accordance with the present invention, it being understood that the number of actuators and structural elements, as well as the spatial disposition of these elements with respect to one another, can vary widely from one embodiment to another. In the particular embodiment depicted, a series of four annular structural elements 202 are illustrated, with three actuators 210 disposed between each pair of structural elements 202.

Figure 3:
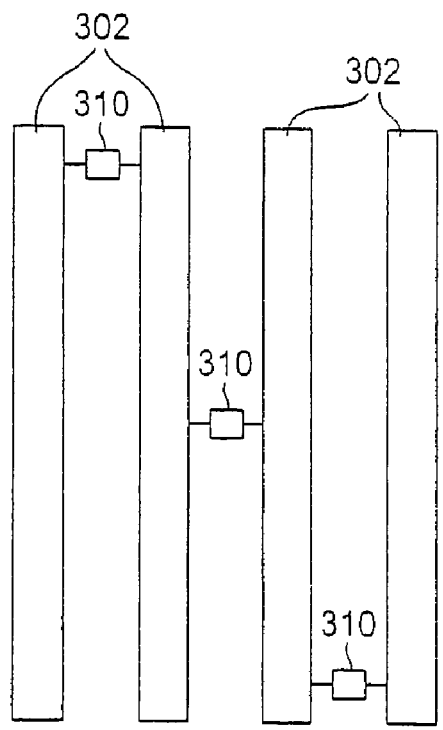

While the assembly depicted in FIG. 2 has the actuators disposed along three parallel axes, numerous variations based upon the above noted considerations are possible. For example, the actuators 310 between structural elements 302 can be deployed in a staggered arrangement as illustrated in FIG. 3.

In general, due to their stiffness and elasticity, the guide catheters of the present invention, like prior art guide catheters, are generally inherently biased toward a substantially linear configuration in the absence of any applied stress. As a result, the catheter can be bent into any number of configurations by simply contracting one or more of the actuators disposed along its length. Once the actuators are relaxed, the guide catheter will assume a more linear configuration.

In alternative designs, multiple actuators can be placed in tension with one another to achieve a desired shape. For example, a series of pivot points can be provided between the structural elements, allowing the catheter to be bent into the desired configuration by placing at least two actuators into tension with one another. Hence, the actuators in a system of this type operate on a principle similar to the operation of skeletal muscles in living organisms such as snakes.

Figure 4:
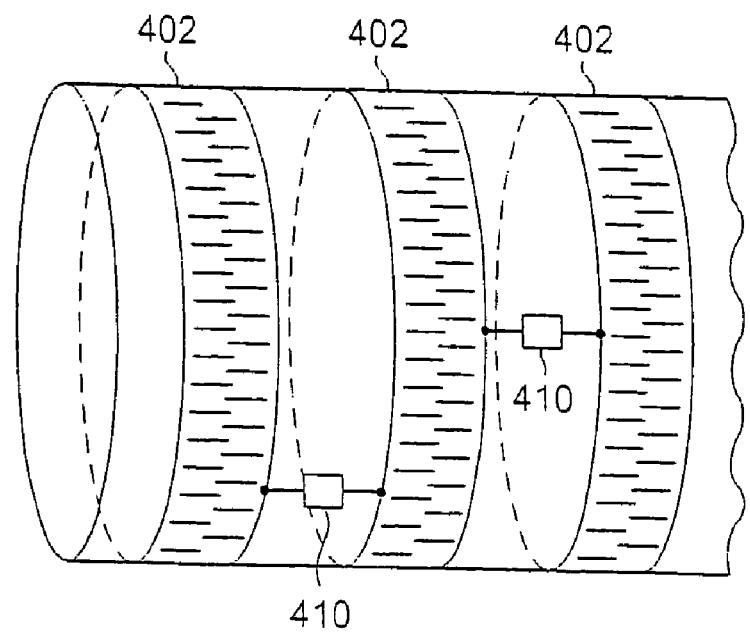

Numerous further variations are possible with respect to guide catheter structural elements. For example, while the structural elements are depicted in FIGS. 2 and 3 as a series of closed loops, the structural elements can also include open loops, akin to the vertebrae structure of a snake. Moreover, the loops can be replaced by tubes of various lengths if desired. For example, a series of short tubes constructed in a fashion similar to known vascular, biliary or esophageal stents can be used. One such structure is illustrated in FIG. 4, in which actuators 410 are positioned between a series of short stent-like elements 402.

The structural elements may also be combined into a unitary structure, such as a single elongated tube. Thus, the discrete loops in some of the embodiments described above may be replaced, for example, by a helical structural element. The actuators can be deployed between adjacent turns of the helix. In this embodiment, that the adjacent turns of the helix act very much like the series of discrete loops depicted, for example, in FIGS. 2 and 3.

Figure 5:
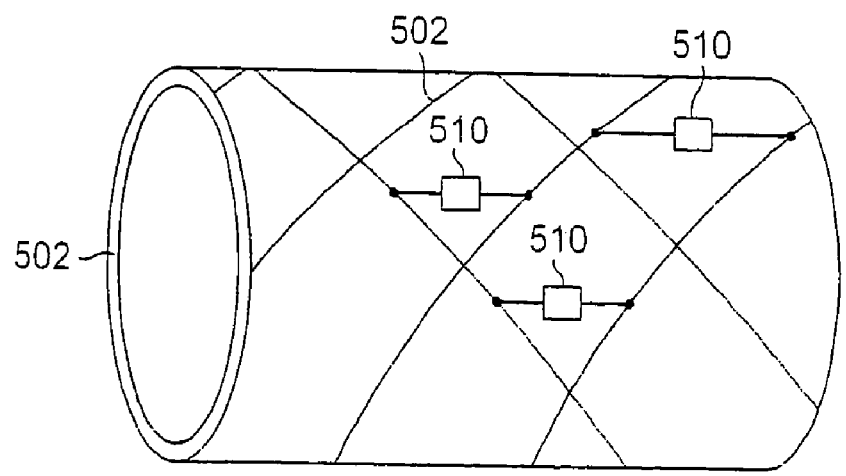

Another example of a unitary structure is illustrated in FIG. 5, which incorporates a stent-like mesh structure 502. Referring to FIG. 5, actuators 510 are disposed between adjacent members of mesh structure 502. The mesh structure 502 is preferably flexible and elastic such that it possesses an inherent bias or memory that acts to restore the assembly to its original (e.g., substantially linear) configuration. Moreover, in the final catheter structure, the mesh structure illustrated will typically have an inner liner and an outer jacket, either or both of which may be elastic in nature, biasing the catheter towards a substantially linear configuration. The actuators 502 can then be used to deflect the structure from this configuration as needed.

In general, the shape of the guide catheters of the present invention can be inferred from the intrinsic position-dependent electrical properties of the electroactive polymer. However, if desired, a number of strain gauges can be employed to provide electronic feedback concerning the orientation of the actuators and structural elements within the assembly. This electronic feedback will also provide a number of additional advantages, including compensation for physiologic changes, greater stability, error correction, and immunity from drift. Strain gauges suitable for use in the present invention include (a) feedback electroactive polymer elements whose impedance or resistance varies as a function of the amount of strain in the device and (b) conventional strain gauges in which the resistance of the device varies as a function of the amount of strain in the device, thus allowing the amount of strain to be readily quantified and monitored. Such strain gauges are commercially available from a number of different sources, including National Instruments Co., Austin, Tex., and include piezoresistive strain gauges (for which resistance varies nonlinearly with strain) and bonded metallic strain gauges (for which resistance typically varies linearly with strain).

Feedback regarding the catheter configuration, as well as the relationship between the catheter and the lumen into which it is inserted, are also readily obtained using radiographic contrast dye as is known in the guide catheter art.

Figure 6A:
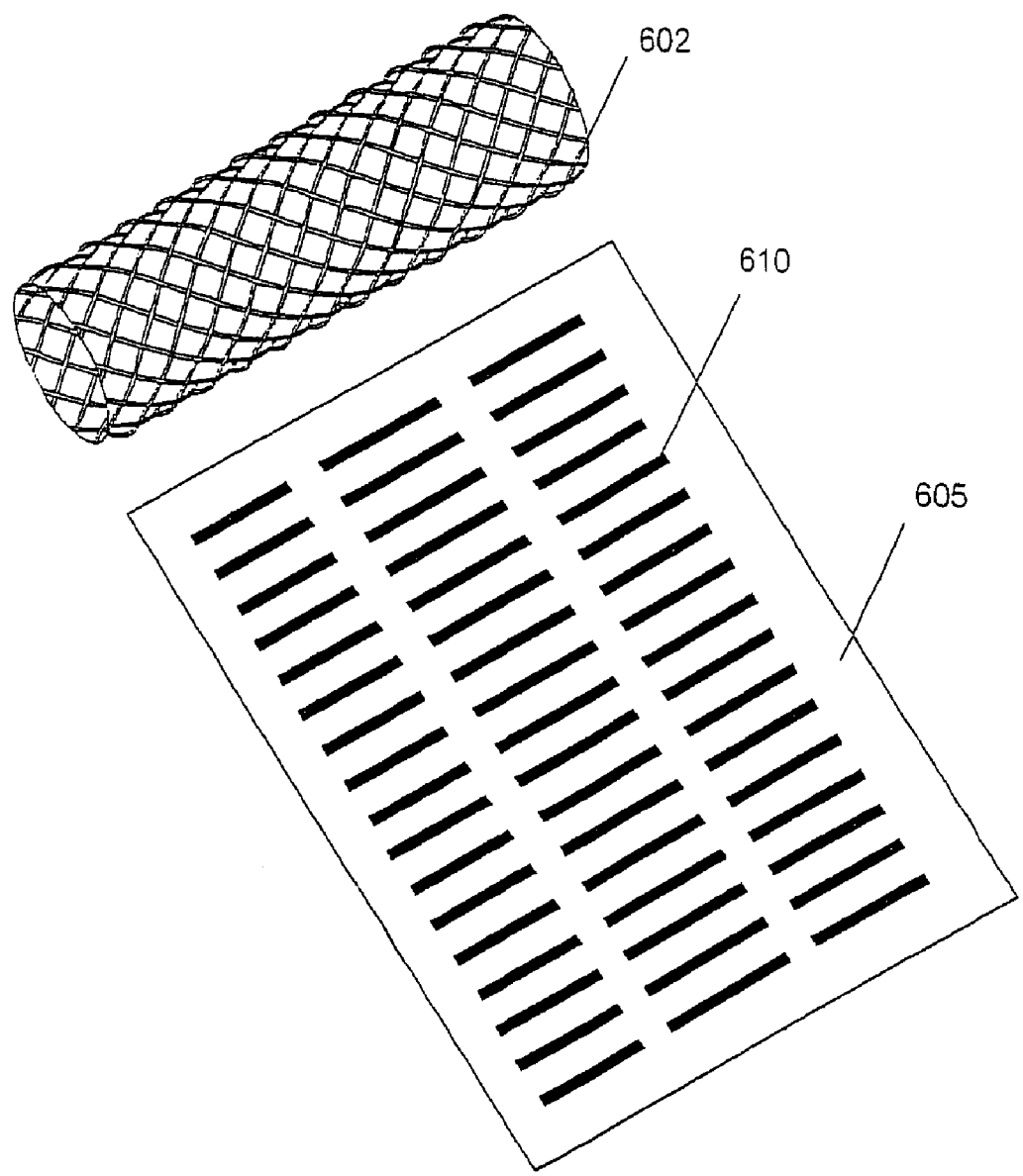
FIGS. 6A and 6B are schematic perspective views, before and after assembly, of a structural element and a substrate layer with associated components, in accordance with an embodiment of the present invention.

In the embodiments described above, the actuators are directly coupled to the structural elements of the guide catheter. However, this need not be the case as illustrated, for example, in FIGS. 6A and 6B. FIG. 6A illustrates a structural element 602, which consists of a braided wire tube, as well as a flexible substrate layer 605. A series of actuators 610 (a single actuator is numbered) is printed on substrate layer 605, along with a control bus (not shown) for transmitting control signals to the actuators 610 from a controlling device.

Figure 6B:
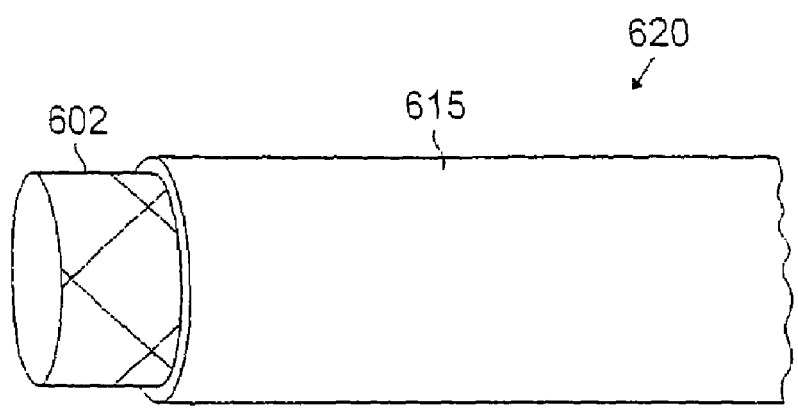

The substrate layer 605 is then wrapped around the structural element 602, and the edges are joined (or overlapped), forming a tubular substrate layer and providing the cylindrical assembly 620 illustrated in FIG. 6B. In this design, the structural element 602 (and in many cases the substrate layer 605) will act to bias the overall assembly 620 toward a preferred configuration, which will typically be a linear configuration. The actuators 610 are used to deflect this structure to the desired degree.

In some embodiments, to the extent that substrate layer 605 is not lubricious, it may be desirable to dispose a lubricious outer jacket (e.g., a hydrogel coating, a silicone, or a fluoropolymers) over the assembly to facilitate advancement of the guide catheter. A lubricious inner liner may also be provided to facilitate passage of an interventional device.

A number of flexible tubular structural elements are known besides the structural element 602 of FIG. 6A–B. For example, numerous flexible tubular structural elements are known from the stent art, including vascular, biliary or esophageal stents. These constructions are typically metal, and include (a) tubular open-mesh networks comprising one or more knitted, woven or braided metallic filaments; (b) tubular interconnected networks of articulable segments; (c) coiled or helical structures (including multiple helices) comprising one or more metallic filaments; (d) patterned tubular metallic sheets (e.g., laser-cut tubes), and so forth.

In addition, known guide catheter configurations frequently consist of an inner liner and an outer jacket, with a flexible tubular structural element (typically metallic, for example, a braided stainless-steel wire tube or a cut stainless steel tube) disposed between the inner liner and outer jacket. As a result, numerous prior art guide catheters are readily adaptable to the present invention by simply incorporating electronic actuators (and strain gauges, if desired) into the structure.

Referring once again to FIGS. 6A and 6B, the substrate layer 605 that is employed in these figures can be selected from a number of flexible materials, and is more preferably formed from one or more polymeric materials. Polymeric materials useful in the construction of the substrate layer 605 include the following polymeric materials: polyolefins such as metallocene catalyzed polyethylenes, polypropylenes, and polybutylenes and copolymers thereof; ethylenic polymers such as polystyrene; ethylenic copolymers such as ethylene vinyl acetate (EVA), butadiene-styrene copolymers and copolymers of ethylene with acrylic acid or methacrylic acid; polyacetals; chloropolymers such as polyvinylchloride (PVC); fluoropolymers such as polytetrafluoroethylene (PTFE); polyesters such as polyethylene terephthalate (PET); polyester-ethers; polysulfones; polyamides such as nylon 6 and nylon 6,6; polyamide ethers such as polyether block amides; polyethers; elastomers such as elastomeric polyurethanes and polyurethane copolymers; silicones; polycarbonates; polychloroprene; nitrile rubber; butyl rubber; polysulfide rubber; cis-1,4-polyisoprene; ethylene propylene terpolymers; as well as mixtures and block or random copolymers of any of the foregoing are non-limiting examples of biostable polymers useful for manufacturing the medical devices of the present invention.

In some embodiments, the substrate layers are constructed from stiff polymers like those used in electronic printed circuits or cables, such as polyimide (e.g., Kapton®), and relieved by selective cutting, e.g. with a laser, to provide the appropriate flexibility.

Materials for guide catheter inner liners and outer jackets can also be selected form the above polymers, as desired.

Although FIG. 6A illustrates a single substrate layer 605, multiple substrate layers can be used. For example, an additional substrate layer can be provided which contains a plurality of strain gauges, for example, feedback polymer elements, along with a readout bus for transmitting information from the strain gauges to a controlling device.

Actuators 610 can be provided on substrate layer 605 in numerous configurations. For example, a single actuator 610 is shown in cross-section in FIG. 6C, disposed on substrate layer 605. As previously discussed, the actuator 610 includes an active member 612 and counter-electrode 618, with an intervening electrolyte-containing layer 614.

As noted above, the active member 612 typically comprises an electroactive polymer, many of which are known in the art. Polypyrrole, polysulfone, and polyaniline are three specific examples. The counter-electrode 618 may be any electrical conductor, for example, another conducting polymer, a conducting polymer gel, or a metal such as gold or platinum, preferably in a flexible form, for example, in the form of a thin layer or foil. The electrolyte within the electrolyte-containing layer 614 can be, for example, a liquid, a gel, or a solid as previously discussed. It is beneficial that the active members 612 avoid contact with the counter-electrode 618 to prevent short-circuiting. In the embodiment illustrated, such contact is prevented by provided the electrolyte within a flexible porous layer of insulating polymer material. Beneficial insulating polymers for this purpose include insulating polymers within the polymer list that is provided above in connection the substrate layer 605. PTFE is a specific example.

Track wires 622a and 622c are connected to active member 612 and counter-electrode 618, respectively, allowing for electrical communication with a controlling device (not shown).

A barrier layer 620 may be provided for several reasons. For example, the barrier layer 620 can prevent species within the electrolyte-containing layer 614 from escaping. Appropriate materials for the barrier layer include those discussed above in connection with substrate layer 605.

Figure 6C:
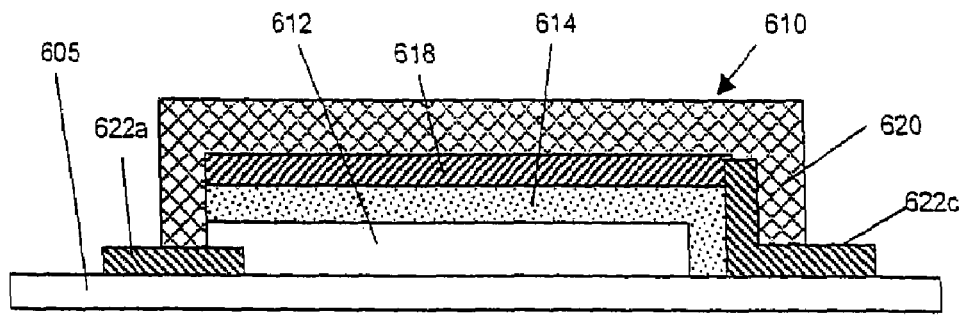
FIGS. 6C–6E are schematic cross sectional views illustrating various actuator configurations, in accordance with three embodiments of the present invention.
Figure 6D:
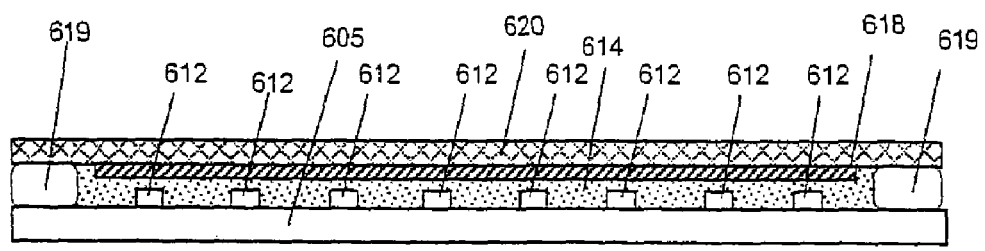

Numerous actuator configurations other than that illustrated in FIG. 6C are also possible. For example, FIG. 6D is a cross-section of eight active members 612 disposed on substrate layer 605. Over the active members are electrolyte-containing layer 614, patterned counter-electrode layer 618 and barrier layer 620. The barrier layer 620 is sealed to the substrate layer 605 using, for example, an adhesive 619. The configuration of FIG. 6D contains a common counter-electrode. The active regions are preferably provided with discrete track wires (not shown) for individual activation.

Figure 6E:
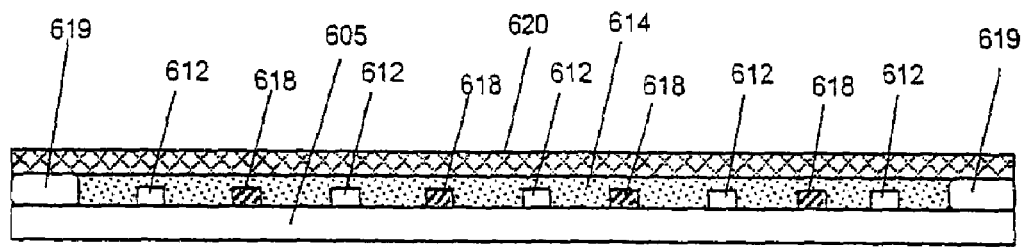

As another example, FIG. 6E is a cross-section including five active members 612 disposed and four counter-electrode regions 618 disposed on a substrate layer 605. An electrolyte-containing layer 614 contacts both the active members 612 and counter-electrode regions 618. A barrier layer 620 is sealed to the substrate layer 605 using, for example, an adhesive 619. The active regions are preferably provided with discrete track wires (not shown) for individual activation. The counter-electrode regions 618 can also be provided with discrete track wires (not shown), or these regions can constitute portions of a single counter-electrode.

Figure 7:
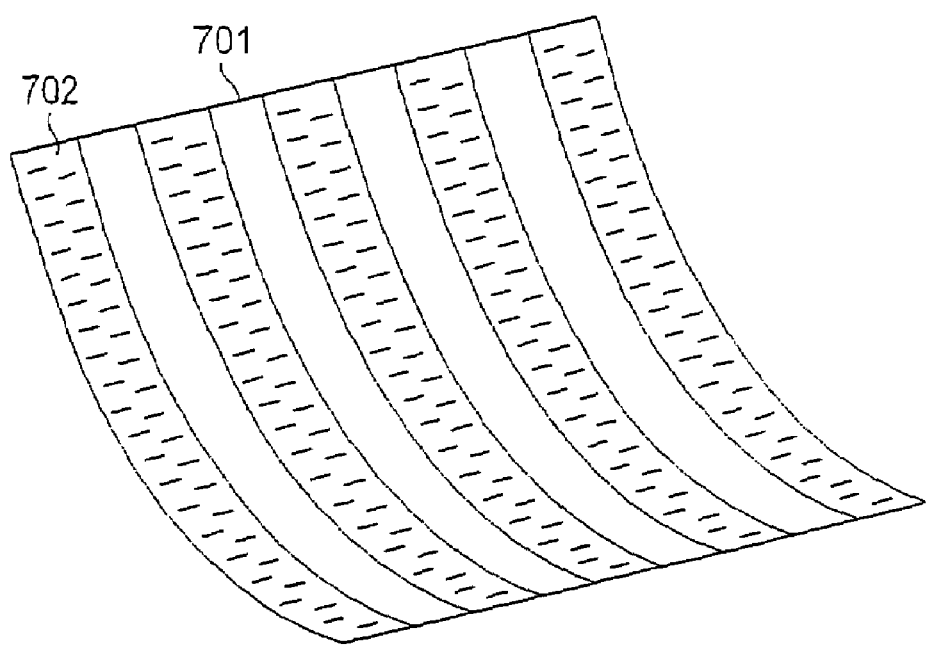
FIG. 7 is a schematic perspective view of a substrate layer with structural elements incorporated therein, in accordance with an embodiment of the present invention.

The structural elements of the guide catheters of the present invention can also be provided on a substrate layer if desired. For example, FIG. 7 illustrates substrate layer 701 having printed thereon a series of relatively stiff structural elements 702 which, when rolled up, will form structural elements similar to those illustrated in FIG. 4.

Figure 8A:
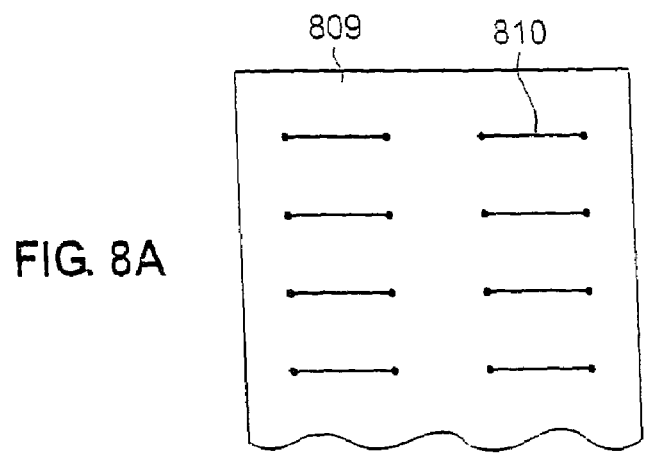
FIGS. 8A–C are schematic plan views illustrating three orientations of actuators on a substrate, in accordance with an embodiment of the present invention.
Figure 8B:
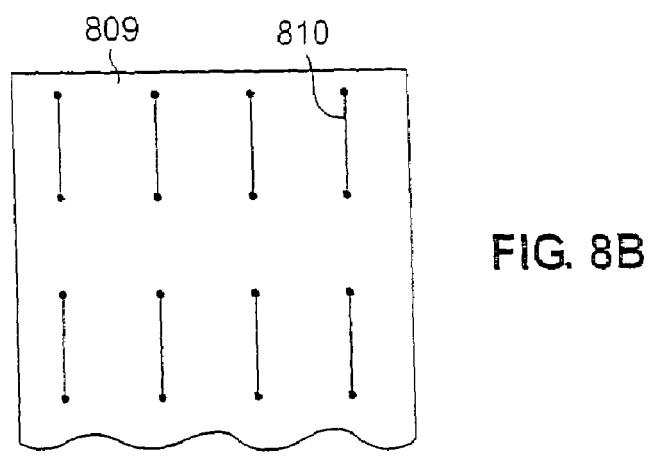
Figure 8C:
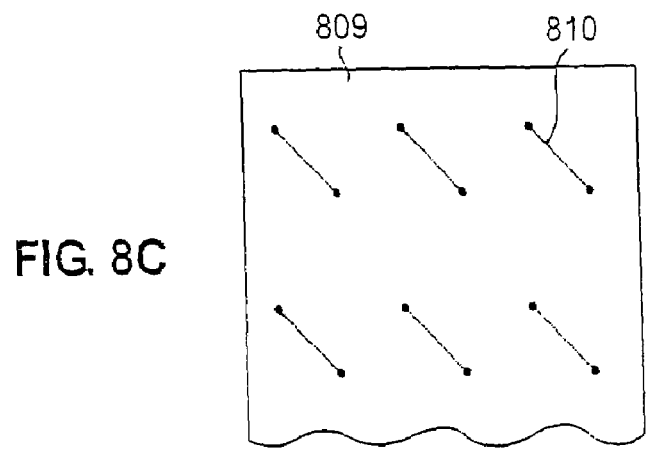

Although the actuators illustrated in the above figures are oriented in the direction of the guide catheter axis, the actuators can be oriented in essentially any direction desired for control. For example, FIGS. 8A, 8B and 8C illustrate three substrate layers 809, each having a series of actuators 810 (one actuator is numbered in each figure), which are oriented in various directions. By laminating these substrate layers together, a laminated structure (not shown) can be created which can bend, contract circumferentially, and so forth.

Each actuator within the guide catheters of the present invention is preferably individually controllable. This allows these elements to be driven for the purpose of effecting changes to the configuration of the overall device. For example, the actuators (and strain gauges, if desired) may be placed in direct communication with a controlling device by means of dedicated circuits linking each of these elements to the device. However, it is more preferred to deploy these elements such that each element is in communication with the controlling device by means of a common communications cable. The signals from each element may be digital or analog. If need be, digital-to-analog or analog-to-digital converters may be provided to convert the signals from one format to the other.

The signals to and from each element may be conveniently managed and transmitted over a common cable by multiplexing. Multiplexing schemes that may be used for this purpose include frequency-division multiplexing, wave-division multiplexing, or time-division multiplexing. Suitable multiplexers and demultiplexers can be employed at each end of the cable and along its length at the position of each actuator or gage.

In terms of electronic data storage, each actuator and strain gauge may be given a separate address in electronic memory where information concerning the state of the element is stored. This information may be accessed to determine the state of the device, or for the purpose of performing operations on the device or its elements. The memory in which the information is stored may be of a volatile or non-volatile type, and may be in the device itself, but is preferably in a separate control and display device (e.g., a personal computer, such as a laptop computer).

Numerous cable configurations are possible. For example, the cables can be directly connected to the actuators. Alternatively, the cables can be printed onto a substrate layer (see, e.g., track wires 622a, 622c illustrated in FIG. 6C). In this case, each substrate layer upon which the actuators (and strain gauges, if desired) are disposed may be similar to a flexible printed circuit board in that the necessary elements are printed upon a flexible substrate. Each layer can be provided with its own track wires and control cables (e.g., the control, and readout, buses discussed above). Alternatively, the actuators and strain gauges can be connected to a separate interconnect layer, for example, by plated through-holes or vias (these also can function as "rivets" to hold the stack of sheets together). Such through-holes can tie into a series of conductive track wires disposed on the interconnect layer, which track wires connect to a "spinal cord", such as a cable bundle, flat cable or ribbon cable that runs the length of the device.

Figure 9:
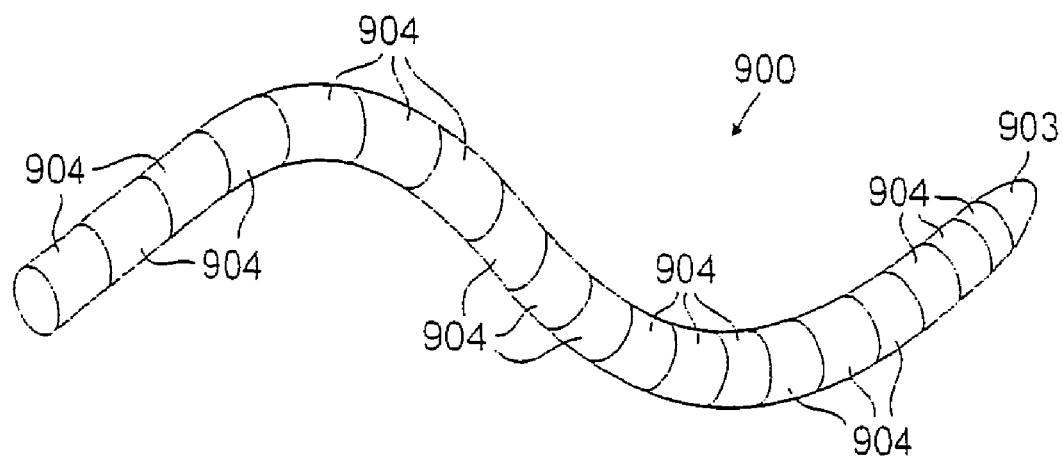
FIG. 9 is a schematic perspective view of a guide catheter in accordance with an embodiment of the present invention.
Figure 10:
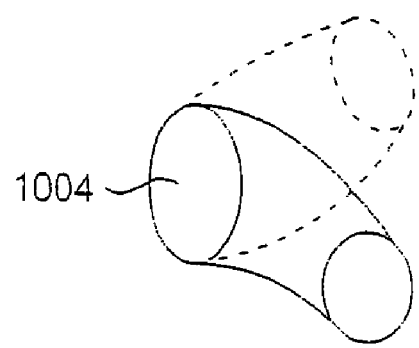
FIG. 10 is a schematic perspective view of a guide catheter module, in accordance with the an embodiment of present invention.

In some embodiments, the guide catheters of the present invention are divided into a series of "deflection modules", each of which includes a plurality of actuators that allow the module to take on a variety of shapes in 3-dimensional space in response to input by the control device. The greater the number of modules, the finer the control of the 3-dimensional orientation of the guide catheter. A simplified schematic diagram of a guide catheter 900 with eighteen modules 904 and a tip 903 (e.g., a soft tip to reduce risk of trauma during catheter advancement) is found in FIG. 9. The overall shape of the guide catheter is established by manipulating the deflection of each of the modules. For example, as illustrated in FIG. 10, the actuators can be activated to deflect a given module 1004 from a first position (designated by solid lines) to a second position (designated by dashed lines). Additional degrees of freedom in deflection are also possible, e.g., changes in diameter or changes in length.

As indicated above, hospital catheterization laboratories presently maintain a large inventory of guide catheters having specific shapes, which allow them to be readily advanced to a site of interest. These large inventories can be drastically reduced using the catheters of the present invention. For example, a controlling device (e.g., lap top computer) can bias the guide catheter actuators to achieve one of a number of pre-selected configurations, resulting in a guide catheter having a desired overall shape. This shape-controlled catheter can then be inserted into a patient (for example, a vertebrate animal, and more preferably a human). If difficulties are encountered, the catheter can be provided with another pre-selected shape using the controlling device, or steered manually or under semiautomatic control based on the guiding images, e.g., from a fluoroscope.

Once a guide catheter reaches its target location (for example, the coronary osteum), a suitable interventional device (for example, an angioplasty device or stent delivery catheter) is inserted through a channel in the guide catheter to access the tissue of interest. Unfortunately, in the prior art, the distal end the guide catheter is prone to dislodgement during the insertion of the interventional device. In accordance with an embodiment of the present invention, the guide catheter is stiffened during interventional device insertion to resist such dislodgement. The catheter can be stiffened all along its length or only over a portion of its length (e.g., at the distal) end in accordance with the invention.

The stiffness of the guide catheter can be adjusted in a number of ways. As a first example, actuators can be disposed within the guide catheter such that they are in tension with one another as discussed above (e.g., in a fashion analogous to skeletal muscles). Such a guide catheter can be stiffened by placing opposing actuators into tension with one another.

In certain embodiments of the invention, the overall shape of the guide catheter is modified based on feedback regarding the catheter configuration, including the relationship between the catheter and the body lumen into which it is inserted. One example of such feedback is a catheter position imaging system that is based on a medical diagnostic image, for example, one provided by radiographic contrast dye (e.g., an angiogram), as is known in the art.

Alternatively, electromagnetic position sensors may be included in the guide catheter structure to provide an electronic readout of the 3D shape and position of the guide catheter, independent of the radiographic images. Such electromagnetic position sensors have been used in animation and metrology, and are presently emerging in cardiology and electrophysiology. Examples of such systems are the NOGA™ cardiology navigation system and the CARTO™ electrophysiology navigation system, both available from Biosense Webster, Diamond Bar, Calif., as well as the RPM Realtime Position Management™ electrophysiology navigation system available from Boston Scientific Corporation, Natick Mass.

In some cases, the guide catheter is provided with a steering system, which is used to control electronic actuators in the guide catheter tip. A number of options are available for catheter steering. For example, the guide catheter can be provided with a manual steering system that is operated under image guidance. Electrical control from the computer can be based, for example, on manual steering input using a joystick or the like. The joystick or the like is manipulated by an operator based, for example, a radiographic contrast dye image.

As another example, based on input from a catheter position imaging sensing system like that discussed above, electrical control can be provided by means of a edge-tracking or center-seeking algorithm to keep the distal end of the guide catheter at or near the center of the body lumen.

In other embodiments, the guide catheter will be steered in a semiautomatic fashion, for example, using a computer algorithm like that discussed above to suggest a direction of travel, with a trained operator acting to either accept or reject the computer-generated suggestion. In this instance, it may be desirable to tailor the algorithm to reflect operator preferences based upon operator profiles.

In other embodiments, the guide catheter system is provided with a shape changing system, which is used to control electronic actuators along the guide catheter length during the insertion process. Numerous options are available.

According to one embodiment, data from strain gauges along the length of the guide catheter can be used to construct a virtual image of the catheter on a display associated with the controlling device (e.g., on the screen of a laptop computer). At the same time, using a catheter position imaging sensing system like that discussed above, an operator can determine a desired shape change for the guide catheter. The operator can then input a desired shape change into the computer, for example, by using a mouse to move virtual onscreen catheter elements to a desired configuration. Subsequently, the computer drives the actuators within the guide catheter to achieve this desired configuration.

In other embodiments, as the guide catheter is advanced into a body lumen, a 3-dimensional representation the desired shape of the guide catheter can be stored into memory, with further data being added with increasing depth of insertion. For example, the orientation of the guide catheter tip (herein referred to as a "lead module") as a function of advancement distance can be stored to the computer, acting as a map for subsequent deflection modules.

Advancement distance data can be provided, for example, from a depth gauge or linear displacement transducer placed at the site of guide catheter introduction. As one specific example, a depth gauge can be supplied, which contains a rotating gear wheel whose revolutions are monitored. As other examples, a linear displacement transducer containing a depth code which can be read optically (using, for example, bar-codes and an optical source and detector) or magnetically (using, for example, a magnetic code and a Hall effect sensor) can be used to determine the extent of guide catheter advancement. These and numerous other known methods are available for determining advancement distance.

The data relating to the orientation of the lead module can be provided, for example, using input from a steering step (e.g., input from a joystick or input from a edge or center-seeking computer algorithm) or from strain gauges.

Using this information, electrical control signals for the actuators are calculated as a function of insertion depth. As a result, as subsequent modules arrive at the position that was previously occupied by the lead module, the actuators within these modules are operated such that they take the orientation of the lead module when it was present at that particular depth of insertion.

Figure 11A:
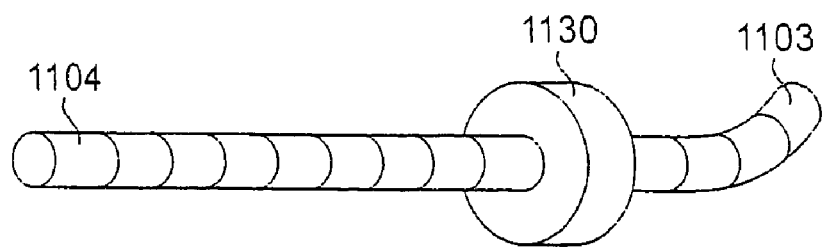
FIGS. 11A–C are schematic perspective views illustrating the ability of the guide catheters of the present invention to retain their orientation at a given depth of insertion.
Figure 11B:
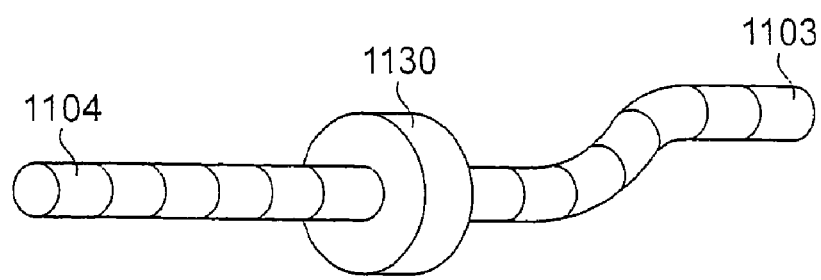
Figure 11C:
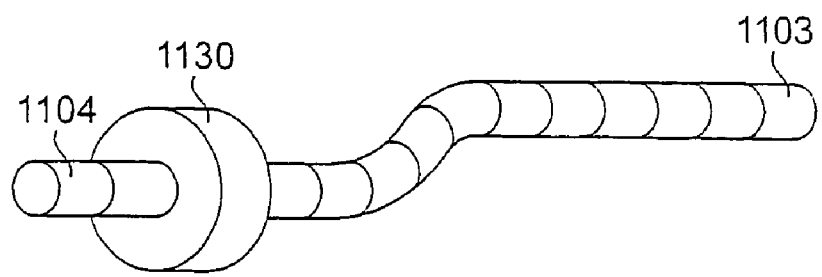

The result of the above is that the guide catheter retains its path in 3-dimensional space, reflecting the shape of the tract (trajectory) that it travels through. This is illustrated in FIGS. 11A–C, which contain simplified schematic diagrams of a guide catheter, consisting of a number of deflection modules 1104 (one numbered) and a lead module 1103, as well as a linear displacement transducer 1130. These figures illustrate the orientation of the guide catheter: shortly after insertion (FIG. 11A), at an intermediate point of insertion (FIG. 11B) and at a point of full insertion (FIG. 11C). As seen from these figures, as it advances, the guide catheter retains its orientation at a given depth of insertion.

Figure 12:
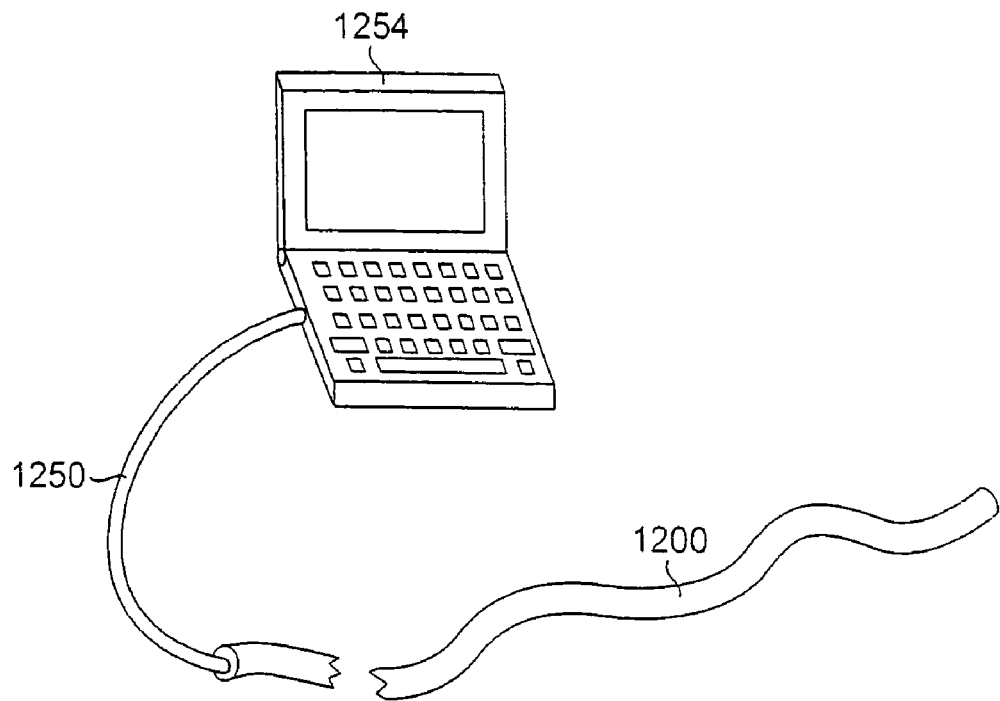
FIG. 12 is a schematic perspective view of a guide catheter apparatus, in accordance with an embodiment of the present invention.

FIG. 12 is a simplified schematic diagram of a guide catheter apparatus in accordance with an embodiment of the invention. The guide catheter apparatus includes a guide catheter portion 1200 containing numerous electronic actuators (not shown) that are controlled by a control unit, such as a computer 1254. An electronic cable bundle 1250 is provided between the guide catheter portion 1200 and an electronic interface, including drivers, which is provided within the computer 1254. Signals are sent from drivers in the electronic interface through cable bundle 1250 to the actuators within the guide catheter portion 1200, controlling the three dimensional shape of the guide catheter portion 1200. If desired, a computer mouse pad or a built-in or peripheral joystick may be used to steer and control the guide catheter portion 1200 as discussed above. In some embodiments of the invention, the guide catheter portion 1200 is provided with strain gauges, in which case signals are output from the strain gauges and sent via the cable bundle 1250 to the electronic interface within the computer 1254. These signals are processed within the computer 1254, for example, to (a) provide the actuators with stability, error correction, and immunity from drift and (b) provide an a virtual image of the guide catheter orientation in vivo, if desired.

Figure 13:
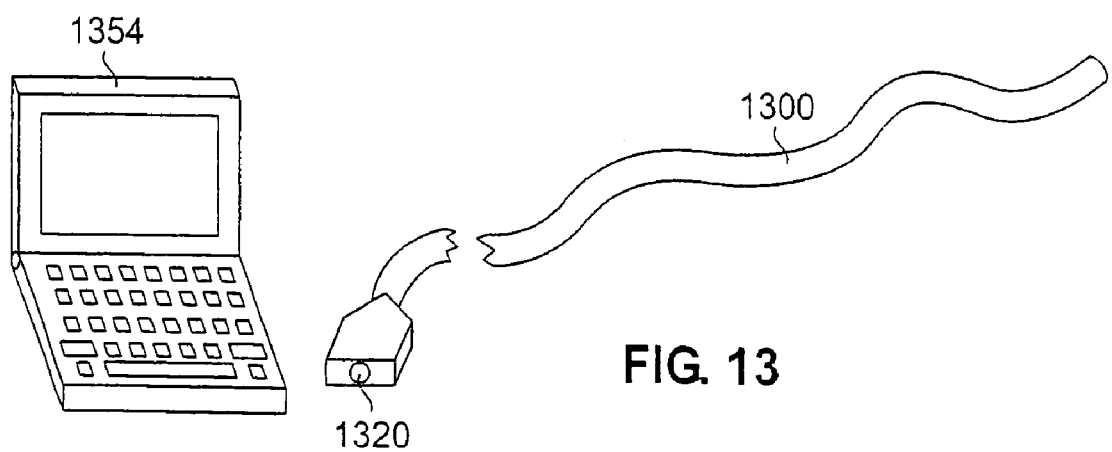
FIG. 13 is a schematic perspective view of a guide catheter apparatus, in accordance with another embodiment of the present invention.

A wireless alternative to the embodiment of FIG. 12 is illustrated in FIG. 13. The guide catheter apparatus illustrated in FIG. 13 includes a guide catheter portion 1300 containing numerous electronic actuators (not shown) that are controlled by a control unit, such as a computer 1354. A power source (not shown), a wireless interface including drivers (not shown), and a working channel 1320 are provided at the proximal end of the guide catheter portion 1300. The wireless interface of the guide catheter portion 1300 communicates with a companion wireless interface within a remote computer 1354.

The guide catheter apparatus of FIG. 13 preferably utilizes wireless interface chipsets, which can be less expensive and more reliable than electrical connectors such as the cable bundle 1250 of FIG. 12. Inexpensive wireless interfaces are presently available from a number of sources, including Bluetooth™ wireless interfaces available from Motorola and IEEE 802.11b wireless interfaces available, for example, from Cisco, Apple and Lucent. Depending on the economics, multiple wireless interfaces can be provided, for example, one for each module of the guide catheter.

The power source for the guide catheter portion 1300 is typically a battery. By building battery power into the guide catheter portion 1300, interconnection cost and complexity are reduced. One or more batteries can be provided essentially anywhere within the guide catheter portion, but are preferably provided at the proximal end of the guide catheter portion 1300, which can be, for example, in the form of an integrated, sealed control handle. The electronics for the wireless interface, including drivers for the electronic actuators and other components, can also be preferably provided at the proximal end of the guide catheter portion 1300.

Figure 14:
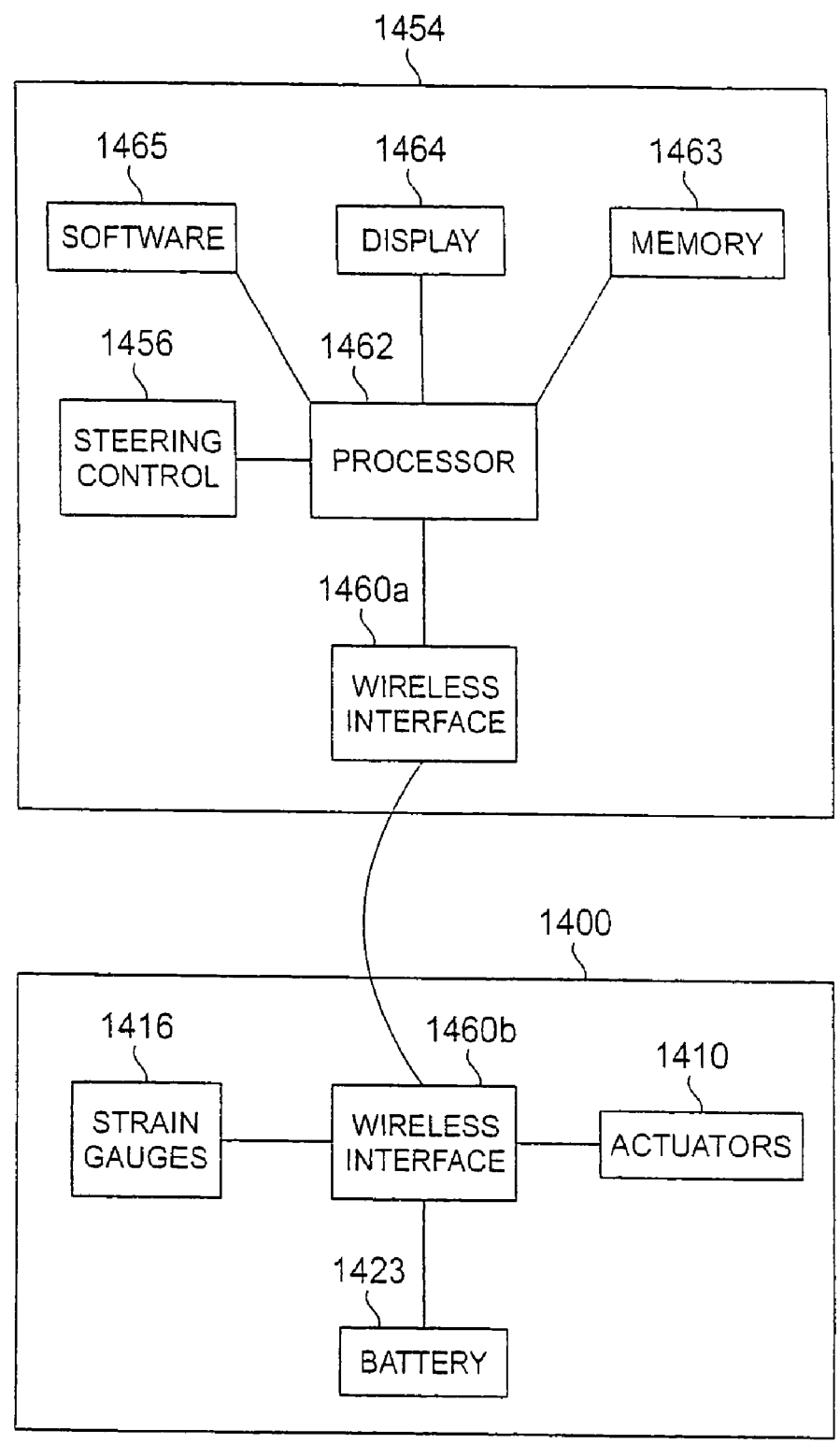
FIG. 14 depicts an exemplary guide catheter apparatus in block diagram format, according to an embodiment of the present invention.

One embodiment of a guide catheter apparatus of the present invention is presented in block diagram format in FIG. 14. The guide catheter apparatus shown includes a guide catheter portion 1400 and a computer 1454. The guide catheter portion 1400 is powered by battery 1423. A wireless interface 1460a and 1460b (including drivers) is provided between the guide catheter portion 1400 and the computer 1454. Control signals for the actuators 1410 within the guide catheter portion 1400 are sent from the computer 1454 to the guide catheter portion 1400 via the wireless interface 1460a, 1460b. At the same time, data (e.g., data from the strain gauges 1416) is also sent from the guide catheter portion 1400 to the computer 1454 via the wireless interface 1460a, 1460b.

As is typical, the computer 1454 contains a processor 1462, memory 1463 and display 1464. If desired, strain gauge data transmitted over the wireless interface 1460a, 1460b can be processed by software 1465 to present a virtual image of the guide catheter portion 1400 on the display 1464 (as an alternative example, a medical diagnostic image, for example, an angiogram, can be presented on the display). The operator can change the configuration of the guide catheter portion 1400, for example, by operating the steering control 1456 (or performing some other operation as discussed above) to provide an input signal that is used by the operating software 1465 (along with any other input signals, such as data from strain gauges, etc.) to calculate a control signal. The control signal is sent to the actuators 1410 in the guide catheter portion 1400 via drivers in the wireless interface 1460b to steer and control the shape of the guide catheter portion 1400.

Although the present invention has been described with respect to several exemplary embodiments, there are many other variations of the above-described embodiments that will be apparent to those skilled in the art, even where elements have not explicitly been designated as exemplary. It is understood that these modifications are within the teaching of the present invention, which is to be limited only by the claims appended hereto.

What is claimed is:

1. A guide catheter apparatus, comprising:
   (a) a guide catheter portion comprising a plurality of electroactive polymer actuators disposed along its axial length, said actuators changing guide catheter portion shape based upon received control signals; and
   (b) a control unit coupled to said plurality of actuators and sending said control signals to said plurality of actuators, wherein each of said plurality of electroactive polymer actuators comprises (a) an active member portion, (b) a counter-electrode portion and (c) a region comprising an electrolyte disposed between said active member portion and said counter-electrode portion, wherein said active member portion, said counter-electrode portion and said region comprising an electrolyte are disposed between a substrate layer and a barrier layer, wherein said substrate layer is in the shape of a tube.

2. The guide catheter apparatus of claim 1, wherein said electroactive polymer actuators comprise an electroactive polymer selected from the group consisting of polyaniline, polypyrrole, polysulfone, and polyacetylene.

3. The guide catheter apparatus of claim 2, wherein said electroactive polymer actuators comprise polypyrrole.

4. The guide catheter apparatus of claim 1, wherein at least a portion of said actuators are in tension with one another.

5. The guide catheter apparatus of claim 1, wherein said plurality of electroactive polymer actuators are disposed along at least 5% of the fully inserted axial length of the guide catheter portion.

6. The guide catheter apparatus of claim 1, wherein said guide catheter portion further comprises a plurality of strain gauges.

7. The guide catheter apparatus of claim 1, wherein said guide catheter portion further comprises a structural element selected from the group consisting of (a) a tubular network comprising at least one metallic filament, (b) a tubular interconnected network of articulable segments, (c) a helical structure comprising at least one metallic filament, and (d) a patterned tubular sheet.

8. The guide catheter apparatus of claim 1, wherein said control signals are sent from said control unit to said actuators over a multiplexed cable.

9. The guide catheter apparatus of claim 1, wherein said control unit comprises a personal computer.

10. The guide catheter apparatus of claim 1, wherein said electroactive polymer actuators are controllable to provide a desired curvature to said guide catheter portion at each of a plurality of loci along the length of said catheter portion.

11. The guide catheter apparatus of claim 1, wherein said control signals correspond to a user selectable shape for said guide catheter portion.

12. The guide catheter apparatus of claim 1, wherein said control unit comprises an electronic memory, and wherein said user selectable shape for said guide catheter portion is stored in said electronic memory.

13. The guide catheter apparatus of claim 1, said control signals are generated using a manual steering device.

14. The guide catheter apparatus of claim 1, wherein said control signals are generated by a shape-generating algorithm within said control unit using medical diagnostic imaging data.

15. The guide catheter apparatus of claim 14, wherein said medical diagnostic imaging data is angiogram data.

16. The guide catheter apparatus of claim 1, wherein said catheter portion comprises a lead module and a plurality of following modules, and wherein said guide catheter portion is adapted to travel in such a way that, when each following module reaches a position previously occupied by said lead module, said actuators cause said each following module to replicate the orientation of said lead module at said position.

17. The guide catheter apparatus of claim 16, wherein position data is provided by a depth gauge or a linear displacement module.

18. The guide catheter apparatus of claim 16, wherein lead module orientation data is provided by strain gauges within said lead module.

19. The guide catheter apparatus of claim 1, wherein said control signals are sent from said control unit to said actuators over a wireless interface.

20. The guide catheter apparatus of claim 1, wherein said plurality of electroactive polymer actuators are disposed along at least 10% of the fully inserted axial length of the guide catheter portion.

21. The guide catheter apparatus of claim 1, wherein said plurality of electroactive polymer actuators are disposed along at least 25% of the fully inserted axial length of the guide catheter portion.

22. The guide catheter apparatus of claim 1, wherein said plurality of electroactive polymer actuators are disposed along at least four centimeters of the guide catheter.

23. The guide catheter apparatus of claim 1 wherein said plurality of electroactive polymer actuators are disposed along at least ten centimeters of the guide catheter.

24. A guide catheter apparatus, comprising:
(a) a guide catheter portion comprising a plurality of electroactive polymer actuators disposed along its axial length, said actuators changing guide catheter portion shape based upon received control signals; and
(b) a control unit coupled to said plurality of actuators and sending said control signals to said plurality of actuators, wherein each of said plurality of electroactive polymer actuators comprises (a) an active member portion, (b) a counter-electrode portion and (c) a region comprising an electrolyte disposed between said active member portion and said counter-electrode portion, wherein said active member portion, said counter-electrode portion and said region comprising an electrolyte are disposed between a substrate layer and a barrier layer, wherein said substrate layer is in the shape of a tube,
wherein at least a portion of said electroactive polymer actuators are adapted to contract in a direction parallel to an axis of said tube.

25. A guide catheter apparatus, comprising:
(a) a guide catheter portion comprising a plurality of electroactive polymer actuators disposed along its axial length, said actuators changing guide catheter portion shape based upon received control signals; and
(b) a control unit coupled to said plurality of actuators and sending said control signals to said plurality of actuators, wherein each of said plurality of electroactive polymer actuators comprises (a) an active member portion, (b) a counter-electrode portion and (c) a region comprising an electrolyte disposed between said active member portion and said counter-electrode portion, and wherein said active member portion, said counter-electrode portion and said region comprising an electrolyte are disposed between a substrate layer and a barrier layer.

* * * * *

UNITED STATES PATENT AND TRADEMARK OFFICE
CERTIFICATE OF CORRECTION

PATENT NO. : 6,997,870 B2 Page 1 of 1
APPLICATION NO. : 10/751544
DATED : February 14, 2006
INVENTOR(S) : Lucien Alfred Couvillon, Jr.

It is certified that error appears in the above-identified patent and that said Letters Patent is hereby corrected as shown below:

Col. 1, line 67, after "curves" insert -- , --.
Col. 1, line 67, after "complex" delete -- , --.
Col. 2, line 2, before "shape", change "user selectable" to -- user-selectable --.
Col. 3, line 32, after "schematic", change "cross sectional" to -- cross-sectional --.
Col. 3, line 44, after "with", delete "the".
Col. 6, line 65, after "embodiment", delete "that".
Col. 8, line 48, after "selected", change "form" to -- from --.
Col. 9, line 10, after "connection", insert -- with --.
Col. 10, line 12, after "or", change "gage" to -- gauge --.
Col. 11, line 11, after "end", insert -- of --.
Col. 11, line 17, change "(e.g., at the distal) end" to -- (e.g., at the distal end) --.
Col. 11, line 54, after "example,", insert -- on --.
Col. 11, line 57, after "position", change "imaging sensing" to -- imaging-sensing --.
Col. 12, line 19, after "representation", insert -- in --.
Col. 13, line 17, after "provide", delete "an".
Col. 13, line 18, after "orientation", change "in vivo" to -- *in vivo* --.

Claim 11, Col. 15, line 8, before "shape", change "user selectable" to -- user-selectable --.
Claim 12, Col. 15, line 12, before "shape", change "user selectable" to -- user-selectable --.
Claim 13, Col. 15, line 14, after "1", insert -- wherein --.

Signed and Sealed this

Eighteenth Day of December, 2007

JON W. DUDAS
*Director of the United States Patent and Trademark Office*